(12) United States Patent
Englert et al.

(10) Patent No.: US 10,167,493 B2
(45) Date of Patent: Jan. 1, 2019

(54) METHODS FOR PRODUCING CAROTENOIDS FROM FERMENTATION BY-PRODUCTS

(71) Applicant: DIREVO Industrial Biotechnology GmbH, Cologne (DE)

(72) Inventors: Joachim Englert, Cologne (DE); Klaudija Milos, Cologne (DE)

(73) Assignee: DIREVO Industrial Biotechnology GmbH, Cologne (DE)

( * ) Notice: Subject to any disclaimer, the term of this patent is extended or adjusted under 35 U.S.C. 154(b) by 297 days.

(21) Appl. No.: 14/891,004

(22) PCT Filed: May 6, 2014

(86) PCT No.: PCT/EP2014/059202
§ 371 (c)(1),
(2) Date: Nov. 13, 2015

(87) PCT Pub. No.: WO2014/184052
PCT Pub. Date: Nov. 20, 2014

(65) Prior Publication Data
US 2016/0083766 A1    Mar. 24, 2016

Related U.S. Application Data

(60) Provisional application No. 61/824,659, filed on May 17, 2013.

(30) Foreign Application Priority Data

May 17, 2013 (EP) .................................. 13168385

(51) Int. Cl.
| | | |
|---|---|---|
| *C12P 23/00* | (2006.01) | |
| *C11B 3/10* | (2006.01) | |
| *C11B 13/00* | (2006.01) | |
| *C07C 403/24* | (2006.01) | |
| *C09B 61/00* | (2006.01) | |
| *C12P 5/00* | (2006.01) | |
| *A23K 20/179* | (2016.01) | |
| *A23K 20/28* | (2016.01) | |

(52) U.S. Cl.
CPC ............ *C12P 23/00* (2013.01); *A23K 20/179* (2016.05); *A23K 20/28* (2016.05); *C07C 403/24* (2013.01); *C09B 61/00* (2013.01); *C11B 3/10* (2013.01); *C11B 13/00* (2013.01); *C12P 5/00* (2013.01); *C07C 2601/16* (2017.05); *Y02W 30/74* (2015.05)

(58) Field of Classification Search
None
See application file for complete search history.

(56) References Cited

U.S. PATENT DOCUMENTS

| | | | |
|---|---|---|---|
| 5,149,549 A | 9/1992 | Beggs | |
| 5,382,714 A | 1/1995 | Khachik | |
| 5,468,701 A * | 11/1995 | Nebergall | ................ B01J 20/12 502/22 |
| 2010/0058649 A1 | 3/2010 | Bootsma | |

FOREIGN PATENT DOCUMENTS

| | | | |
|---|---|---|---|
| EP | 0611071 A1 | 8/1994 | |
| JP | 2002223787 A | 8/2002 | |
| WO | WO-2013052357 A2 * | 4/2013 | ........... A23K 1/1756 |

OTHER PUBLICATIONS

Proctor, Andrew, and Sevugan Palaniappan. "Soy oil lutein adsorption by rice hull ash." Journal of the American Oil Chemists' Society 66.11 (1989): 1618-1621.*
Singh, N., and M. Cheryan. "Extraction of oil from corn distillers dried grains with solubles." Transactions of the ASAE 41.6 (1998): 1775. (Year: 1998).*
PCT/EP2014/059202 International Search Report dated Aug. 25, 2014.
Boki, Keito. "Bleaching of Alkali-refined Vegetable Oils with Clay Minerals." Journal of the American Oil Chemists' Society, Mar. 1, 1992, 69(3):232-236, Springer, DE.

* cited by examiner

*Primary Examiner* — Robert J Yamasaki
(74) *Attorney, Agent, or Firm* — Wagenknecht IP Law Group PC

(57) ABSTRACT

The present technology relates to methods for extracting carotenoids like β-carotene or lutein from oil obtained from/as a by-product derived from a feedstock material like starch-containing material in a processes for producing fermentation products by-products derived from a fermentative production process, in particular from an ethanol fermentation process, wherein the by-product is selected from the group consisting of distillers' wet grain (DWG), distillers' dried grains (DDG), distillers' solubles (DS), distillers' dried solubles (DDS), distillers' dried grain with solubles (DDGS), and mixtures thereof.

6 Claims, 3 Drawing Sheets

METHODS FOR PRODUCING CAROTENOIDS FROM FERMENTATION BY-PRODUCTS

CROSS-REFERENCE TO RELATED APPLICATIONS

This application is a U.S. National stage of PCT/EP2014/059202 filed on May 6, 2014, which claims priority to U.S. Provisional Application Ser. No. 61/824,659 filed on May 17, 2013 and EP Application Serial No. 13168385.6 filed on May 17, 2013, each of which is incorporated herein by reference in its entirety.

FIELD OF THE INVENTION

The present disclosure relates to methods for extracting carotenoids like ß-carotene or lutein from oil obtained from/as a by-product derived from a feedstock material like starch-containing material in a processes for producing fermentation products by-products derived from a fermentative production process, in particular from an ethanol fermentation process, wherein the by-product is selected from the group consisting of distillers' wet grain (DWG), distillers' dried grains (DDG), distillers' solubles (DS), distillers' dried solubles (DDS), distillers' dried grain with solubles (DDGS), and mixtures thereof.

BACKGROUND OF THE DISCLOSURE

Carotenoids are synthesized de novo in bacteria, algae, fungi and plants. Carotenoids are a class of natural fat-soluble pigments found principally in plants, algae, and photosynthetic bacteria, where they play a critical role in the photosynthetic process. They also occur in some non-photosynthetic bacteria, yeasts, and molds, where they may carry out a protective function against damage by light and oxygen. Although animals appear to be incapable of synthesizing carotenoids, many animals incorporate carotenoids from their diet. Within animals, carotenoids provide bright coloration, serve as antioxidants, and can be a source for vitamin A activity (Ong and Tee 1992; Britton et al. 1995).

Carotenoids are responsible for many of the red, orange, and yellow hues of plant leaves, fruits, and flowers, as well as the colors of some birds, insects, fish, and crustaceans. Some familiar examples of carotenoid coloration are the oranges of carrots and citrus fruits, the reds of peppers and tomatoes, and the pinks of flamingoes and salmon (Pfander 1992). Some 600 different carotenoids are known to occur naturally (Ong and Tee 1992), and new carotenoids continue to be identified (Mercadante 1999).

Carotenoids are defined by their chemical structure. The majority carotenoids are derived from a 40-carbon polyene chain, which could be considered the backbone of the molecule. This chain may be terminated by cyclic end-groups (rings) and may be complemented with oxygen-containing functional groups. The hydrocarbon carotenoids are known as carotenes, while oxygenated derivatives of these hydrocarbons are known as xanthophylls. Beta-carotene, the principal carotenoid in carrots, is a familiar carotene, while Lutein, the major yellow pigment of marigold petals, is a common xanthophyll.

The structure of a carotenoid ultimately determines what potential biological function(s) that pigment may have. The distinctive pattern of alternating single and double bonds in the polyene backbone of carotenoids is what allows them to absorb excess energy from other molecules, while the nature of the specific end groups on carotenoids may influence their polarity.

The economic importance of carotene compounds in general and in particular ß-carotene and lutein has increased steadily in recent times. Industry has attempted to respond to the stimulated demand on the one hand by synthethic production of carotenoids and on the other hand by extracting and subsequently crystallizing carotenoids from natural sources. The consumers in accordance with their present critical attitude towards synthetic products have a clear preference for natural ß-carotene and lutein.

ß-Carotene for example is a vitamin A precursor and thus an important constituent in food, feed and cosmetic applications. It further serves as a pigmenting substance in many fields, such as, for example, in the beverages industry. Pure carotenoid crystals derived from Marigold flowers, comprising predominantly of Xanthophylls such as Lutein, Zeaxanthin and Cryptoxanthin and low levels of beta-carotene have been proven scientifically to reduce the risk of age related macular degeneration (Reference: Moeller S M, Jacques P F, Blumberg J B "The potential role of dietary Xanthophylls in cataract and age related macular degeneration," Journal of the American College of Nutrition, 2000; 19: 522S-527S), control over LDL cholesterol (Reference: Chopra M., Thurnham D I, "Effect of Lutein on oxidation of low density lipoproteins (LDL) in vitro", Proceedings of the Nutrition Society, 1994; 53: 1993, #18A.), prevention of Coronary heart diseases (Reference: Howard A N, Williams N R, Palmer C R, Cambou J P, Evans A E, Foote J W, et al., "Do hydroxy-carotenoids prevent coronary heart disease?" A comparison between Belfast and Toulouse, "International Journal of Vitamin and Nutrition Research, 1996; 66: 113-118) and free radicals scavenging and immunity enhancing (Reference: Chew B P, Wong M W, Wong T S, "Effects of Lutein from Marigold extract on immunity and growth of mammary tumors in mice," Anticancer Research, 1996; 16: 3689-3694). Lutein, (beta-e-carotene-3-3'-diol) and Zeaxanthin (beta-beta-carotene-3-3'-diol) belong to Xanthophylls group in the carotenoids family with highly reactive hydroxyl groups which cannot be synthesized by humans and animals.

Whereas until recently only the "classical" natural ß-carotene sources such as e.g. carrots or algae were available for commercial isolation processes, innovative biotechnological approaches have nowadays exploited a considerably more suitable profound source using fermentative methods. The fermentation of particular filamentous fungi has enabled a concentration of up to more than 5% by weight ß-carotene to be achieved in the dried fermentation biomass; the concentration of ß-carotene is therefore about ten higher than in the traditional natural sources.

In general, the induction of ß-carotene crystallization by adding solvents invariably leads to high yields, however, it is necessary to add large amounts of solvent as described for n-propanol for example in the U.S. Pat. No. 1,988,031 in order to obtain a satisfying yield. When extracting from natural materials using organic solvents such as e.g. petroleum ether (cf. the U.S. Pat. Nos. 1,967,121 and 1,998,031) there is generally the problem that, due to the low solubility of ß-carotene, and in particular in the case of high ß-carotene concentrations, an extremely large amount of solvent must be selected which, however, in turn considerably and negatively effects the space-time yield.

Recently, several processes have been described in which ß-carotene is extracted from natural materials using supercritical carbon dioxide at very high process pressures (U.S.

Pat. No. 4,400,398). Despite the good extraction results a general disadvantage of this gas extraction process is the complicated technical implementation of the required high pressure, which is generally more cost-intensive than processes which operate under normal pressure.

U.S. Pat. No. 5,382,714 reports that saponified marigold oleoresin from Kemin Industries (Des Moines, Iowa) containing free lutein is the preferred starting material for the isolation of pure lutein. The saponification step involves high percentage of propylene glycol and the saponification time is done for a minimum period of three hours subjecting the product to heat for prolonged period, which increases the process time too.

Within the framework of the unification of the food law legislation within the EU, a draft of a guideline to lay down specific purity criteria for dyes, which can be used in foods, was submitted to the commission in January 1995. In this document the solvents acetone, methyl-ethylketone, methanol, ethanol, propan-2-ol, hexane, dichloromethane and carbon dioxide are proposed for extracting natural carotenes. However, with the exception of dichloromethane, these solvents are less suitable for economic extraction from natural materials in which ß-carotene occurs in high concentrations due to their low dissolving capacity for ß-carotene. On the other hand a forward-looking food industry should refrain from using dichloromethane for ecological and consumer-related reasons.

The object of the present invention is therefore to provide novel methods for isolating carotenes, in particular ß-carotene and/or lutein, from new natural sources and in particular from solid natural materials which circumvents the disadvantages of the known processes, in particular for the use as animal feed ingredients.

SUMMARY OF THE DISCLOSURE

The present disclosure relates to methods for extracting carotenoids like ß-carotene or lutein from oil obtained from/as a by-product derived from starch-containing material in a processes for producing fermentation products by-products derived from a fermentative production process, in particular from an ethanol fermentation process, wherein the by-product is the oil itself or the by-product is selected from the group consisting of distillers' wet grain (DWG), distillers' dried grains (DDG), distillers' solubles (DS), distillers' dried solubles (DDS), distillers' dried grain with solubles (DDGS), and mixtures thereof.

In one aspect, the present disclosure pertains to methods for extracting a carotenoid from oil obtained from/as a by-product derived from starch-containing material in a processes for producing fermentation products comprising the steps of a) contacting the oil and/or the oil-containing by-product with a solid adsorption material, b) separating the solid adsorption material containing the carotenoid, and c) extracting the carotenoid from the solid adsorption material.

In a further aspect, the present disclosure relates to methods of manufacturing an animal feed additive comprising a carotenoid bound to a solid adsorption material, wherein the carotenoid is derived from oil obtained from/as a by-product derived from starch-containing material in a processes for producing fermentation products comprising the steps of a) contacting the oil or the oil-containing by-product with a solid adsorption material and b) separating the solid adsorption material containing the carotenoid.

Furthermore, aspects of the present disclosure relate to animal feed ingredients comprising a carotenoid derived from oil obtained from/as a by-product derived from starch-containing material in a process for producing fermentation products.

In a further aspect, the present disclosure relates to a process for the extraction of a carotenoid from oil obtained from/as a by-product derived from starch-containing material in a process for producing fermentation products by extracting the carotenoid with a solid adsorption material.

Furthermore, aspects of the present disclosure relates to the use of bentonite containing a carotenoid derived from oil obtained from a by-product derived from starch-containing material in a process for producing fermentation products as an animal feed ingredients.

Furthermore, aspects of the present disclosure relates to the use of bentonite containing a carotenoid as an animal feed additive.

DETAILED DESCRIPTION OF THE DISCLOSURE

Figure 1:
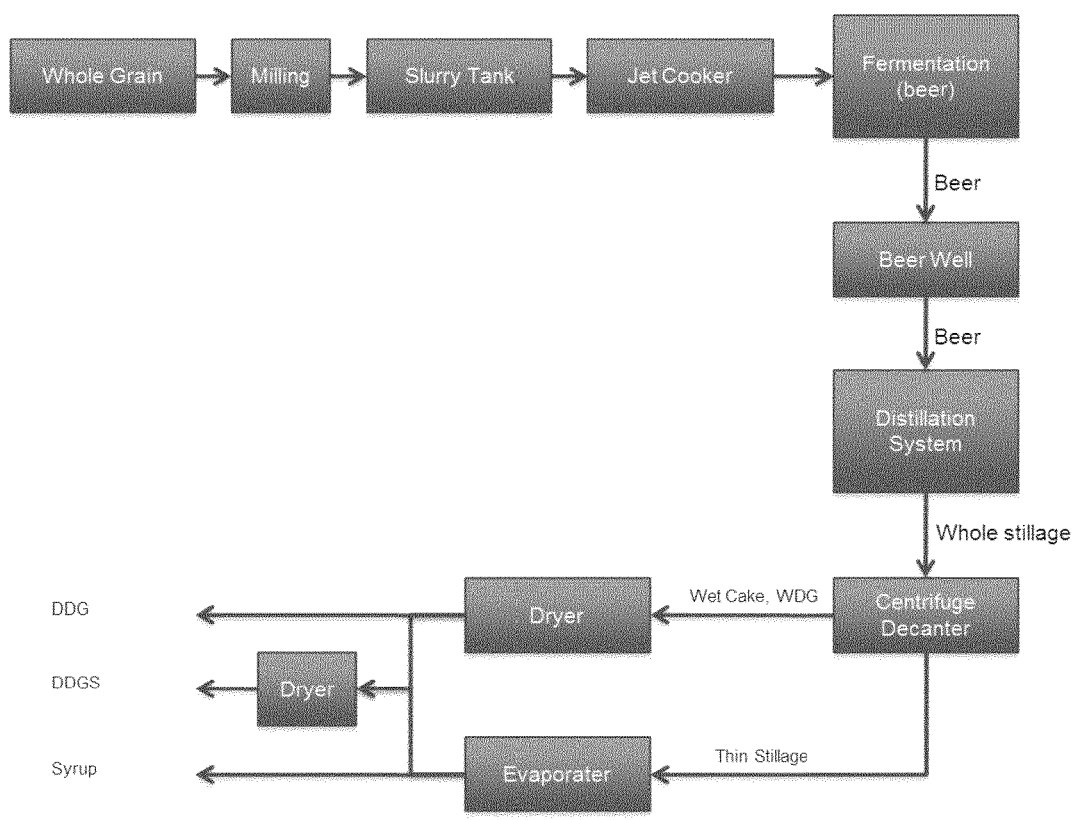
FIG. 1 schematically shows an ethanol production process.

The object of the present invention is to provide novel methods for isolating carotenoids, in particular ß-carotene and/or lutein, from new natural sources.

Fermentation products, such as ethanol, are produced by first degrading starch-containing material into fermentable sugars by liquefaction and saccharification and then converting the sugars directly or indirectly into the desired fermentation product using a fermenting organism. Liquid fermentation products such as ethanol are recovered from the fermented mash (often referred to as "beer" or "beer mash"), e.g., by distillation, which separate the desired fermentation product from other liquids and/or solids. The remaining faction, referred to as "whole stillage", is dewatered and separated into a solid and a liquid phase, e.g., by centrifugation. The solid phase is referred to as "wet cake" (or "wet grains" or "WDG") and the liquid phase (supernatant) is referred to as "thin stillage". Dewatered wet cake is dried to provide "Distillers Dried Grains" (DDG) used as nutrient in animal feed. Thin stillage is typically evaporated to provide condensate and syrup (or "thick stillage") or may alternatively be recycled directly to the slurry tank as "backset". Condensate may either be forwarded to a methanator before being discharged or may be recycled to the slurry tank. The syrup consisting mainly of limit dextrins and non-fermentable sugars may be blended into DDG or added to the wet cake before drying to produce DDGS (Distillers Dried Grain with Solubles).

It is known to commercially use the various byproducts and residues derived from the fermentation processes like the ethanol production process. Distillers residues or byproducts, as well as by-products of cereal and other food industry manufacturing, are known to have a certain value as sources of protein and energy for animal feed. Furthermore, the oil from the by-products like DDGS-oil can be recovered as a separate by-product for use in biodiesel production or other biorenewable products are sought. The color of the by-products originated from the carotenoid in the basic raw material like corn. For example, DDGS has yellow color originated from carotenoid in corn. In some advantageous embodiments, the by-product is the arising oil itself or the by-product is selected from the group consisting of distillers' wet grain (DWG), distillers' dried grains (DDG), distillers' solubles (DS), distillers' dried solubles (DDS), distillers' dried grain with solubles (DDGS), and mixtures thereof. For example, though DDGS as byproduct is referenced herein with respect to the methods and materials described, it is to be understood that for example distillers dried grains (DDG) could also be utilized. In particular, DDG retain significant oil content, and in embodiments of the processes and methods described herein DDG may be used in place of DDGS.

Methods for dewatering stillage and for extracting oil arising from a fermentation process are known in the art. These methods include decanting or otherwise separating the whole stillage into wet cake and thin stillage. See, e.g., U.S. Pat. Nos. 6,433,146, 7,601,858, and 7,608,729, and U.S. Application Publication No. 2010/0058649. Furthermore, the thin stillage can be evaporated or condensed into syrup or thick stillage from which the oil can be extracted utilizing centrifugation, filtering, heat, high temperature, increased pressure, or a combination of the same. Another way to extract oil is to lower the pH of the thin stillage or syrup. The use of surfactants to break emulsions also enhances oil extraction. Further methods of extracting crude corn oil from corn DDGS are discussed in Sing et. al., "Extraction of Oil From Corn Distillers Dried Grains with Solubles", Transactions of the ASAE 41 (6), 1775-1777 (1998), the teachings of which are incorporated by reference herein.

After de-oiling of the by-products the carotenoids from the starch-containing materials are mainly comprised in the oil. Surprisingly, the inventors found that with solid adsorption materials like bentonite or silica the carotenoid can be easily extracted from the oil, in particular directly in the ethanol production plant and then extracted from the adsorption material for further processing or uses of the adsorption material comprising carotenoids, in particular ß-carotene and/or lutein bound to the adsorption material, in particular to bentonite which may directly be used as an animal feed ingredient.

In addition to the advantages of the adsorption properties of carotenoids to bentonite or other adsorption materials, and therefore their new generated value in animal nutrition, there are several additional technical effects. After extraction of the carotenoids, the oil has a higher quality and pureness, directly processed in the fermentation plant itself. This results in an improved quality of the DDGS-oil and therefore in a higher prize these companies can demand. Nevertheless an improved quality can obtain new markets for a cheap, pure corn oil, such as animal nutrition and food, cosmetics and healthcare, optimized/-improved biodiesel producing processes and many more.

As mentioned above, commercially valuable amounts of oil can be extracted from the byproducts like the DDG and DDGS using a solvent extraction process. From the solvent extracted oil the carotenoids can be extracted by methods according to the resent disclosure and the oil can then be further processed to provide, for example, food grade oil, such as food grade corn oil where the DDG and DDGS are derived from an ethanol biorefinery that utilizes corn grain as biomass. Alternatively, the oil extracted from the byproducts like DDG and DDGS can be subjected to a transesterification process to yield biodiesel and glycerin.

Solid adsorption materials according to the present disclosure may be a silicate such bentonite, calcium bentonite, sodium bentonite, perlite, verxite, or zeolite. Bentonite is a naturally occurring mineral consisting primarily of the tri-layered aluminum silicate, montmorillonite. It may contain calcium or sodium as the predominant available or exchange ion. Bentonite is normally used or intended for use in non-medicated animal feed as an anti-caking agent or a pelleting aid.

Bentonite is an absorbent aluminium phyllosilicate, essentially impure clay consisting mostly of montmorillonite. As mentioned above, there are different types of bentonite, each named after the respective dominant element, such as potassium (K), sodium (Na), calcium (Ca), and aluminium (Al). Bentonite usually forms from weathering of volcanic ash, most often in the presence of water. However, the term bentonite, as well as a similar clay called tonstein, has been used to describe clay beds of uncertain origin. For industrial purposes, two main classes of bentonite exist: sodium and calcium bentonite. In stratigraphy and tephrochronology, completely devitrified (weathered volcanic glass) ash-fall beds are commonly referred to as K-bentonites when the dominant clay species is illite. Other common clay species, and sometimes dominant, are montmorillonite and kaolinite. Kaolinite-dominated clays are commonly referred to as tonsteins and are typically associated with coal.

It is an advantage of bentoite that it can be used as an animal feed additive since it is not toxic or has an unwanted side effect to the animals. For example, U.S. Pat. No. 5,149,549 teaches the use of a montmorillonite clay, particularly a bentonite clay, admixed with animal feeds as a mycotoxin binder.

U.S. Pat. No. 5,165,946 teaches the use of a montmorillonite clay in combination with a suitable sequestrant, particularly phosphate and polyphosphate salts, as a mycotoxin binder. U.S. Pat. No. 5,639,492 further refines the art, teaching the use of acid-activated calcium bentonite clay admixed with animal feeds to reduce effects of mycotoxin contamination.

As mentioned above, carotenoids are exemplary, highly-beneficial nutrients that animal feeds often naturally lack. Carotenoids are tetraterpenoid organic pigments that are naturally occurring in the chloroplasts and chromoplasts of certain plants and certain bacteria. Carotenoids can function as anticarcinogens, immunomodulators, natural colorants, and cell membrane stabilizers. Even though most animals are incapable of producing carotenoids, animals are generally able to assimilate ingested carotenoids and employ them in various ways in metabolism. Thus, animals must obtain these desired carotenoids through their diet.

The term "carotenoids" as used herein includes beta-carotene and lutein, which are desirable fortifying nutrients as most animals are generally incapable of synthesizing these materials. Importantly, the carotenoids produced are natural mixtures of stereoisomers of the individual carotenoids, as opposed to a single isomer that is most commonly produced with artificially synthesized carotenoids.

Some embodiments pertains to methods for extracting a carotenoid from oil obtained from/as a by-product derived from starch-containing material in a processes for producing fermentation products comprising the steps of:

i) Converting starch containing material to fermentable sugars ii) Fermentation of the fermentable sugars with a microorganism iii) Separation of the by-product iv) Recovering the oil from/as the by-product v) Contacting the oil and/or the oil-containing by-product with a solid adsorption material vi) Separating the solid adsorption material containing the oil vii) Extracting the carotenoid from the adsorption material The conversion of starch containing material to fermentable sugars may include liquefaction and saccharification. The liquefaction may be carried out in the presence of an alpha-amylase, preferably a bacterial alpha-amylase or acid fungal alpha-amylase. In an embodiment, a pullulanase, isoamylase, and/or phytase is added during liquefaction. The fermenting organism is preferably a yeast, e.g., a strain of *Saccharomyces cerevisiae*. Suitable fermenting organisms may be any organism, including bacterial and fungal organisms, suitable for use in a fermentation process and capable of producing a desired fermentation product. The fermenting organism may be a C6 or C5 fermenting organism, or a combination thereof. Both C5 and C6 fermenting organisms are well known in the art. Suitable fermenting organisms are able to ferment, i.e., convert, fermentable sugars, such as arabinose, fructose, galactose, glucose, maltose, mannose, and/or xylose, directly or indirectly into the desired fermentation product.

As mentioned above, the fermenting organism is preferably yeast, e.g., a strain of *Saccharomyces cerevisiae* or *Saccharomyces diastaticus*. In an avantegeous embodiment a yeast strain of *Saccharomyces diastaticus* is used (SIHA Amyloferm®, E. Begerow GmbH&Co, Langenlonsheim, Germany) since their exo-amylase activity can split liquid starch and also dextrin, maltose and melibiose.

Liquefaction may be carried out as a three-step hot slurry process. The slurry is heated to between 60-95° C., preferably 80-85° C., and an alpha-amylase is added to initiate liquefaction (thinning). Then the slurry may be jet-cooked at a temperature between 95-140° C., preferably 105-125° C., for about 1-15 minutes, preferably for about 3-10 minutes, especially around about 5 minutes. The slurry is cooled to 60-95° C. and more alpha-amylase is added to complete the hydrolysis (secondary liquefaction). The liquefaction process is usually carried out at a pH of 4.0 to 6.5, in particular at a pH of 4.5 to 6.

Saccharification may be carried out using conditions well known in the art with a saccharifying enzyme, e.g., beta-amylase, glucoamylase or maltogenic amylase, and optionally a debranching enzyme, such as an isoamylase or a pullulanase. For instance, a full saccharification process may last up to from about 24 to about 72 hours, however, it is common to do a pre-saccharification for typically 40-90 minutes at a temperature between 30-65° C., typically about 60° C., followed by complete saccharification during fermentation in a simultaneous saccharification and fermentation process (SSF process). Saccharification is typically carried out at a temperature from 20-75° C., preferably from 40-70° C., typically around 60° C., and at a pH between 4 and 5, normally at about pH 4.5.

The most widely used process to produce a fermentation product, especially ethanol, is the simultaneous saccharification and fermentation (SSF) process, in which there is no holding stage for the saccharification, meaning that a fermenting organism, such as a yeast, and enzyme(s), including the hemicellulase(s) and/or endoglucanase(s), may be added together. SSF is typically carried out at a temperature from 25° C. to 40° C., such as from 28° C. to 35° C., from 30° C. to 34° C., preferably around about 32° C. In an embodiment, fermentation is ongoing for 6 to 120 hours, in particular 24 to 96 hours.

Any suitable feedstock material comprising carotenoids may be used in the present invention. The feedstock for producing the fermentation product may be any starch- and/or sugar containing material, preferably starch- and/or sugar containing plant material, including: sugar cane, tubers, roots, whole grain; and any combination thereof.

The starch-containing material may be obtained from cereals. Suitable starch-containing material includes corn (maize), wheat, barley, cassava, sorghum, rye, triticale, or any combination thereof.

Corn is the preferred feedstock, especially when the fermentation product is ethanol. The starch-containing material may also consist of or comprise, e.g., a side stream from starch processing, e.g., C6 carbohydrate containing process streams that may not be suited for production of syrups. Beer components include fiber, hull, germ, oil and protein components from the starch-containing feedstock as well as non-fermented starch, yeasts, yeast cell walls and residuals. Production of a fermentation product is typically divided into the following main process stages: a) Reducing the particle size of starch-containing material, e.g., by dry or wet milling; b) Cooking the starch-containing material in aqueous slurry to gelatinize the starch, c) Liquefying the gelatinized starch-containing material in order to break down the starch (by hydrolysis) into maltodextrins (dextrins); d) Saccharifying the maltodextrins (dextrins) to produce low molecular sugars (e.g., DP1-2) that can be metabolized by a fermenting organism; e) Fermenting the saccharified material using a suitable fermenting organism directly or indirectly converting low molecular sugars into the desired fermentation product; f) Recovering the fermentation product, e.g., by distillation in order to separate the fermentation product from the fermentation mash.

The term "fermentation product" means a product produced by a process including a fermentation step using a fermenting organism. Fermentation products include alcohols (e.g., arabinitol, n-butanol, isobutanol, ethanol, glycerol, methanol, ethylene glycol, 1,3-propanediol [propylene glycol], butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); isoprene; polyketide; gases (e.g., methane, hydrogen (H2), carbon dioxide (CO2), and carbon monoxide (CO)); antibiotics (e.g., penicillin and tetracycline); enzymes; vitamins (e.g., riboflavin, B12, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes include alcohol fermentation processes. In an embodiment, the fermentation product is ethanol, which may be used as fuel ethanol or as potable ethanol.

Following the completion of the fermentation process, the material remaining is considered the whole stillage. As used herein, the term "whole stillage" includes the material that remains at the end of the fermentation process both before and after recovery of the fermentation product, e.g., ethanol. The fermentation product can optionally be recovered by any method known in the art. In one embodiment, the whole stillage is separated or partitioned into a solid and liquid phase by one or more methods for separating the thin stillage from the wet cake. Such methods include, for example, centrifugation and decanting. The fermentation product can be optionally recovered before or after the whole stillage is separated into a solid and liquid phase.

The fermentation product may be recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation as mentioned above. Ethanol with a purity of up to about 96 vol. % can be obtained, which can be used as, for example, fuel ethanol, drinking ethanol, i.e., potable neutral spirits, or industrial ethanol.

In an embodiment, the aqueous by-product (whole stillage) from the distillation process is separated into two fractions, e.g., by centrifugation: wet grain (solid phase), and thin stillage (supernatant). In another embodiment, the methods of the disclosure further comprise separation of the whole stillage produced by distillation into wet grain and thin stillage; and recycling thin stillage to the starch containing material prior to liquefaction. In one embodiment, the thin stillage is recycled to the milled whole grain slurry. The wet grain fraction may be dried, typically in a drum dryer. The dried product is referred to as distillers dried grains, and can be used as mentioned above as high quality animal feed. The thin stillage fraction may be evaporated providing two fractions (see FIG. 1 and FIG. 2), (i) a condensate fraction of 4-6% DS (mainly of starch, proteins, and cell wall components), and (ii) a syrup fraction, mainly consisting of limit dextrins and non-fermentable sugars, which may be introduced into a dryer together with the wet grains (from the whole stillage separation step) to provide a product referred to as distillers dried grain with solubles, which also can be used as animal feed. Thin stillage is the term used for the supernatant of the centrifugation of the whole stillage. Typically, the thin stillage contains 4-6% DS (mainly starch and proteins) and has a temperature of about 60-90° C. In another embodiment, the thin stillage is not recycled, but the condensate stream of evaporated thin stillage is recycled to the slurry containing the milled whole grain to be jet cooked.

Further details on how to carry out liquefaction, saccharification, fermentation, distillation, and recovering of ethanol are well known to the skilled person.

After separation of a byproduct, the byproduct may be de-oiled if the by-product is not the oil itself. As mentioned above, methods for extracting oil from the process, in particular from the fermentation byproducts are known in the art. For example, the thin stillage can be evaporated or condensed into syrup or thick stillage from which the oil can be extracted utilizing centrifugation, filtering, heat, high temperature, increased pressure, or a combination of the same.

After recovering of the oil from/as the by-product, the oil is contacted with a solid adsorption material as described above and may be incubated for a sufficient time. After incubation, the solid adsorption material containing the oil is separated.

For the extraction of the carotenoid from the solid adsorption material prepared as described here, different organic solvents can be used. The solvent extraction may be carried out with a suitable hydrocarbon, such as hexane; various chlorinated solvents such as trichloroethylene or perchloroethylene; alcohols, such as methanol, ethanol, or isopropanol; ketones, such as acetone or methyl ethyl ketone; and various mixtures of these and other similar solvents. This disclosure relates to the use of food-grade solvents considered as natural or mixtures thereof which present reasonably high solubility for the carotenoid components, which are admissible for both pharmaceutical and food applications. These solvents can be recovered and reused. Preferably, solvents such as but not limited to hexane and tert-butylmethyl ether are used.

However as mentioned above, the solid adsorption material, in particular bentonite may be also directly used as an animal feed additive comprising very pure carotenoids. The bentonite is not toxic and the bound carotenoids are digestible and useable for the animals (see Example C). Therefore, the above described methods according to the present disclosure are easy animal feed additive production processes.

The inventions described and claimed herein are not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control. Various references are cited herein, the disclosures of which are incorporated by reference in their entireties. The present invention is further described by the following examples, which should not be construed as limiting the scope of the invention.

EXAMPLES

In the following examples, materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

A) Preparation of DDGS-Oil for Lutein Adsorption

Crude oil was obtained as a by-product from an Ethanol Plant. First step was to remove water soluble impurities e.g. Lecithin, free fatty acids for mucus reduction by different washing steps (100 ml 10% $H_3PO_4$/|DDGS-Oil, 3×100 ml fresh tap water/|DDGS-oil, distilled water). The phases were separated by storing the flask at 90° C. for one hour, the organic phase was treated further, and the aqueous phase was discarded. The Oil was heated up to 150° C. under vacuum for several hours to remove residual impurities and for final clarification. The cleared DDGS-Oil was stored at 4° C.

B) Lutein Adsorption by Bentonites and other Potential Adsorption Materials

Defined quantities (e.g. 50 mg, 100 mg, 200 mg) of adsorption material/ml DDGS-oil was weighted into a 10 ml round bottom flask. 5 ml of DDGS-oil was added. A vacuum of at least 5 mbar was applied to the flask. The sample was equilibrated for at least 5 min until the initial bubble forming activity extenuates. The flask was further incubated under vacuum at 120° C. for 1 h. The received oil-product was filtered through a coarse-filter to remove the loaded adsorption material from the oil-phase.

The remaining adsorption of the oil was determined with a Tecan M1000 microplate reader at λ=447 nm to evaluate the absorption capacity of the used adsorbance. Dilutions were performed using purified commercially available maize-oil. Typical values for residual carotenoid adsorptions, depending on the adsorption materials, can be found in table1. Table 1 shows typical normalized values of remaining adsorption after carotenoid adsorption. The corrected adsorption represents the value of the total extracted carotenoid related to the raw material.

TABLE 1

Typical normalized values of remaining adsorption after carotenoid adsorption

| Sample | Adsorption | Corrected adsorption (Control) |
| --- | --- | --- |
| Untreated Oil | 100% | /// |
| Control (no adsorption material) | −19.64% | 0.0% |
| Bentonite 50 mg/ml | −48.35% | 28.7% |
| Bentonite 200 mg/ml | −95.64% | 76.0% |
| Sipernate 50 mg/ml | −25.41% | 5.8% |
| Sipernate 200 mg/ml | −71.84% | 52.2% |
| Semolina bran 50 mg/ml | −18.13% | −1.5% |

The loaded adsorption material was spread over filter-paper and dried at 90° C. in a cabinet drier for 48 h.

Figure 2:
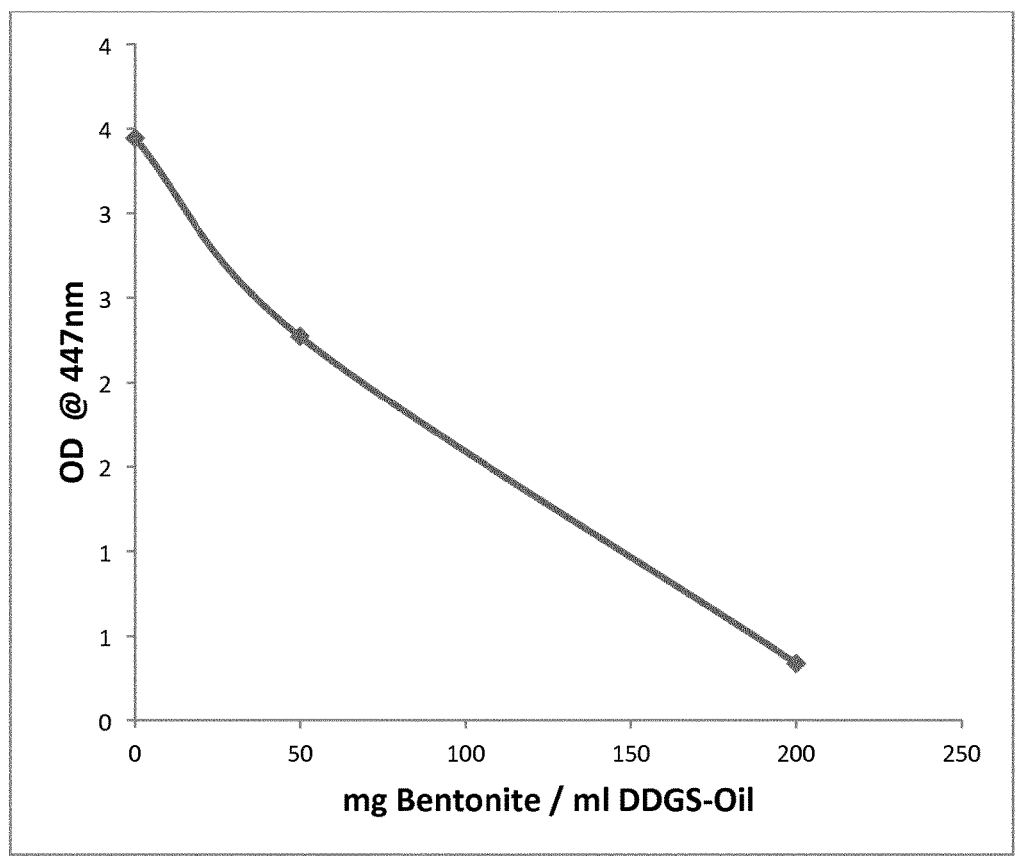
FIG. 2 is a calibration curve representing the degrees of adsorbance at 447 nm.

The calibration curve in FIG. 1 represents the degree of adsorbance at 447 nm with the increase of used Bentonite mass per milliliter of used DDGS-oil (see also Table 2).

TABLE 2

Bentonite concentration

| mg Bentonite/g DDGS-Oil | OD @ 447 nm |
| --- | --- |
| 0 | 3.442 |
| 50 | 2.270 |
| 200 | 0.340 |

C) In-vitro Assay for Releasing of Carotenoides Bound to Adsorption Materials

To guarantee the digestibility and usability of Lutein, bound to appropriate adsorption materials, an in-vitro assay was performed with samples of Lutein-loaded samples.

For this reason 2.5 g of Lutein-loaded adsorption Material was incubated with 10.25 ml 115 mM HCl for 30 Minutes. 1 ml of a 115 mM HCl/Pepsin (6000 U/ml) solution was added and after another 30 min 3.5 ml of destilled water. 30 Minutes the reaction was neutralized with 1.4 ml of a 0.39 M NaOH solution. After another incubation time of 30 minutes 0.84 ml of a 16 mg/ml Pancreation solution in 1M NaHCO3, including 10 mM Bile salts, was added. 5 hours later the reaction was stopped by cooling the reaction mixture down to 4° C. All incubation steps were performed at 40° C. in a shaking incubator at 150 prm. As a negative control an aliquot with acid and base but without enzymes was taken along the procedure. A second negative control was the incubation of 2.5 g of adsorption material in distilled water.

D) Determination of Re-Purgeable Lutein via Fatty-Soluble Determination

For the determination of the released Lutein-oil from the adsorption material the cooled reaction mixture was centrifuged at 3800× g for 30 min. The samples were overlayed with 5 ml n-Hexane cautious to obtain the released Lutein from the surface. The n-Hexan-Phase was collected in a preweighted flask, the procedure was repeated two times. After evaporating the collected Hexan-Phases with a rotary evaporator at 80° C. and 200 mbar for 10 minutes the flasks were incubated for 24 h at 90° C. in a heat chamber to equilibrate before weighting.

Figure 3:
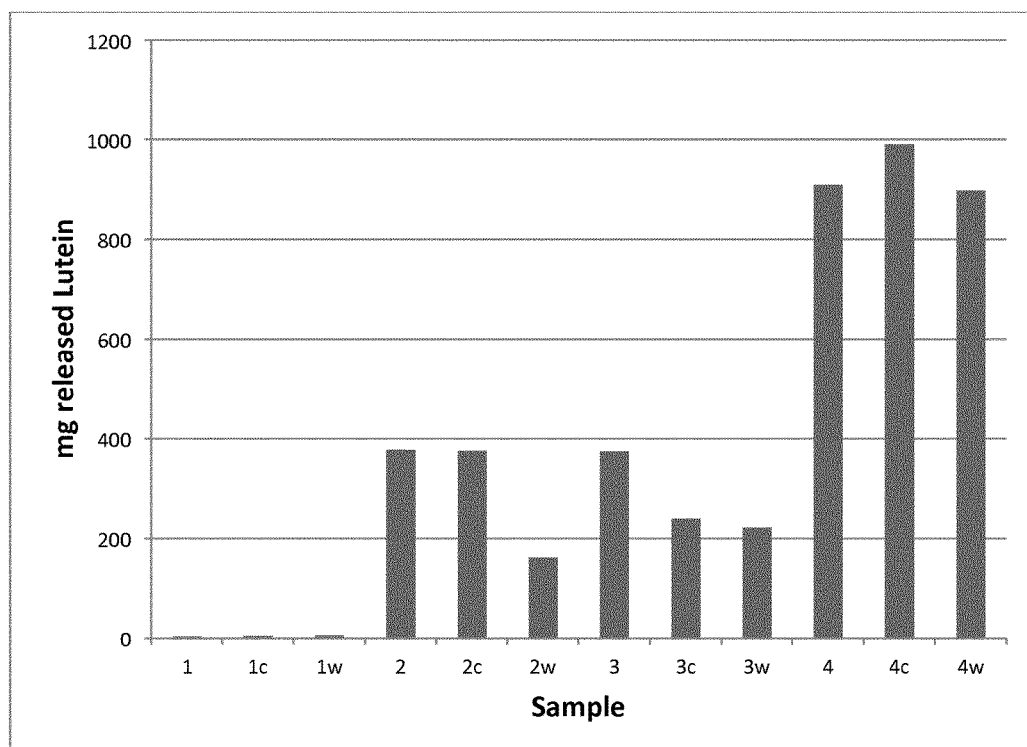
FIG. 3 is a diagram showing the results of the n-Hexan extraction of different adsorption materials.

With the received data from the in-vitro-digest (see Table 3) it could be shown that Luteine, bound to adsorption materials can be desorbt during the digestion process in animals and therefore these food grade adsorption materials are a good source for Carotenoid-supply in animal nutrition. In Table 3, the abbreviation "c" means control without bile salts or enzymes and "w" means control without bile salts or enzymes, without acid or base. Table 2 and FIG. 3 shows the results of the n-Hexan extraction of different adsorption materials, in particular the desorption behavior of Lutein from adsorption materials during in-vitro-digest.

TABLE 2

Results of the n-Hexan extraction of different adsorption materials.

| Sample | | Flask | Dried Sample | released Oil after in-vitro digestion [mg] |
| --- | --- | --- | --- | --- |
| 1 | Lutein-loaded | 15.2152 | 15.2186 | 3.4 |
| 1c | Bentonite dried | 17.6302 | 17.6348 | 4.6 |
| 1w | | 17.4174 | 17.4227 | 5.3 |
| 2 | Lutein-loaded | 18.026 | 18.4026 | 376.6 |
| 2c | Bentonite wet | 17.1915 | 17.5666 | 375.1 |
| 2w | | 17.0789 | 17.2401 | 161.2 |
| 3 | Lutein-loaded | 16.9525 | 17.3257 | 373.2 |
| 3c | Sipernat | 16.9 | 17.1392 | 239.2 |
| 3w | dried | 16.7212 | 16.9427 | 221.5 |
| 4 | Lutein-loaded | 17.3629 | 18.2717 | 908.8 |
| 4c | Sipernat wet | 16.8853 | 17.875 | 989.7 |
| 4w | | 16.963 | 17.86 | 897 |

The data shown in Table 3 and FIG. 3 proves that Carotenoides bound to Bentonites can be released during an In-vitro digestion. Comparison with control samples (c & w) show that the desorbtion process can be supported by enzymes. Furthermore the release of Carotenoides can be supported by the change the pH-Value. Finally there can be observed that the drying-process after the adsorption step seems to have a great influence on the desorption ability of carotenoids from the adsorption material. Anomalies within the decrease of Carotenoid desorption in dataset 4, 4c and 4w are caused by the inconsistent loading of the wet adsorption material.

What is claimed is:

1. A method for extracting a carotenoid for use in animal feed, wherein said method comprises the steps of:
   a) converting starch containing material to fermentable sugars;
   b) fermenting said fermentable sugars with a microorganism;
   c) separating a by-product from said fermentation;
   d) recovering oil from said by-product;
   e) contacting said oil with a solid adsorption material;
   f) separating said solid adsorption material from said oil;
   g) extracting a carotenoid from said adsorption material using tert butyl methyl ether; and h) introducing said extracted carotenoid as an ingredient into animal feed.

2. The method according to claim 1, wherein the carotenoid to be extracted is a ß-carotene or lutein.

3. The method according to claim 1, wherein the by-product is selected from the group consisting of distillers' wet grain (DWG), distillers' dried grains (DDG), distillers' solubles (DS), distillers' dried solubles (DDS), distillers' dried grain with solubles (DDGS), and mixtures thereof.

4. The method according to claim 1, wherein the fermentation is an ethanol production process.

5. The method according to claim 1, wherein the starch-containing material is selected from the group consisting of corn, wheat, barley, triticale, cassava, sorghum, rye, and a combination thereof.

6. The method according to claim 1, wherein the solid adsorption material is a silica or bentonite.

\* \* \* \* \*